US008956667B2

(12) United States Patent
Roy et al.

(10) Patent No.: US 8,956,667 B2
(45) Date of Patent: Feb. 17, 2015

(54) METHODS OF IDENTIFYING POTENTIAL COMPONENTS FOR TARGETED DRUG DELIVERY COMPOSITIONS

(75) Inventors: Josee Roy, Memphis, TN (US); Victor Kelley, Cordova, TN (US); Roger E. Harrington, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 672 days.

(21) Appl. No.: 12/731,822

(22) Filed: Mar. 25, 2010

(65) Prior Publication Data

US 2010/0247683 A1    Sep. 30, 2010

Related U.S. Application Data

(60) Provisional application No. 61/163,565, filed on Mar. 26, 2009.

(51) Int. Cl.
*A61K 33/06* (2006.01)
*A61K 33/14* (2006.01)
*A61K 47/48* (2006.01)

(52) U.S. Cl.
CPC ............ *A61K 33/06* (2013.01); *A61K 47/48215* (2013.01)
USPC ........................................................ 424/722

(58) Field of Classification Search
None
See application file for complete search history.

(56) References Cited

U.S. PATENT DOCUMENTS

| | | | |
|---|---|---|---|
| 3,026,248 A | 3/1962 | Noseworthy et al. | |
| 4,020,162 A | 4/1977 | Ghilardi et al. | |
| 4,451,447 A | 5/1984 | Kaplan et al. | |
| 5,328,992 A * | 7/1994 | Peter et al. ................. | 534/16 |
| 5,605,687 A | 2/1997 | Lee et al. | |
| 7,582,680 B1 | 9/2009 | Shi et al. | |
| 7,837,987 B2 | 11/2010 | Shi et al. | |
| 2003/0118545 A1 | 6/2003 | Shi et al. | |
| 2004/0214790 A1 | 10/2004 | Borgens | |
| 2005/0069520 A1 | 3/2005 | Shi et al. | |
| 2007/0048853 A1 * | 3/2007 | Benz et al. ................. | 435/193 |

FOREIGN PATENT DOCUMENTS

| | | |
|---|---|---|
| FR | 2657623 A1 | 8/1991 |
| GB | 1250304 A | 10/1971 |
| GB | 1286351 A | 8/1972 |
| WO | WO0128544 A | 4/2001 |
| WO | 02092107 | 11/2002 |

OTHER PUBLICATIONS

Zheng et al. "Crystal Structure of the Catalytic Subunit of CAMP-Dependent Protein Kinase Complexed with MgATP and Peptide Inhibitor," Biochemistry 1993, 32, pp. 2154-2161.*

Physical properties accessed on Mar. 28, 2013 at http://www.elmhurst.edu/~chm/vchembook/160Aintermolec.html.*

Nishiyama et al. "Cisplatin-Loaded Polymer-Metal Complex Micelle with Time-Modulated Decaying Property as a Novel Drug Delivery System," Pharmaceutical Research 2001, vol. 18, No. 7, pp. 1035-1041.*

Maltesh et al. "Effect of Binding of Cations to Polyethylene Glycol on Its Interactions with Sodium Dodecyl Sulfate," Langmuir 1992, 8, pp. 1926-1930.*

Horikoshi et al. Vibrational spectra and conformation of polyethyleneglycol complexed with calcium and magnesium chlorides, Journal of Molecular Structure, Oct. 15, 1990, vol. 239, pp. 33-42.*

Simpson et al., "Intrathecal magnesium sulfate protects the spinal cord from ischemic injury during thoracic aortic cross-clamping,"; Anesthesiology (1994) vol. 81, pp. 1493-1499.

Lang-Lazdunski et al., "Prevention of ischemic spinal cord injury: comparative effects of magnesium sulfate and riluzole,"Journal of Vascular Surgery (Jul. 2000); vol. 32; No. 1; pp. 179-189.

Ancill, R.J., "The blood volume of the normal guinea-pig," J. Physiol. (1956)I32, pp. 469-475.

Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.

Borgens R B and Bohnert D., "Rapid recovery from spinal cord injury after subcutaneously administered polytheylene glycol," Journal of Neuroscience Research (2001); vol. 66, pp. 1179-1186.

Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.

The International Search Report and The Written Opinion of the International Searching Authority in PCT/US2007/067580, Dec. 4, 2007.

Turner, et al., "Magnesium gluconate offers no more protection than magnesium sulphate following diffuse traumatic brain injury in rats.", Journal of the American College of Nutrition. 23(51 (2004), 541S-544S.

Muir, et al., "Magnesium for acute stroke (Intravenous Magnesium Efficacy in Stroke trial): randomised controlled trial.". The Lancet, 363(9407). (Feb. 7, 2004). 439-45.

(Continued)

*Primary Examiner* — Abigail Fisher
*Assistant Examiner* — Jessica Kassa
(74) *Attorney, Agent, or Firm* — Sorell Lenna & Schmidt LLP

(57) ABSTRACT

Methods of preparing compositions for preferential distribution of active agents to injury sites are provided. The compositions may comprise a polymer with hydrophilic properties and one or more active agents, such as compounds comprising hydrophilic metal ions. Because the delivery ligand and the active agent are specifically selected so the interactions between them are mainly of an ionic nature. Methods of identifying suitable components for such compositions are also disclosed.

12 Claims, No Drawings

(56) References Cited

OTHER PUBLICATIONS

Saver, et al., "Prehospital Neuroprotective Therapy for Acute Stroke: Results of the Field Administration of Stroke Therapy-Magnesium (FAST-MAG) Pilot Trial.", Stroke, 35(5). (2004). 106-108.
Bittner, et al., "Reconnection of severed nerve axons with polyethylene glvcol.". Brain Research, 367(1-2), (1986), 351-355.
McIntosh, et al., "Magnesium protects against neurological deficit after brain injury.". Brain Research. 482(2). (1989). 252-260.
Shapiro, et al., "Oscillating field stimulation for complete spinal cord injury in humans: a Phase 1 trial.", J. Neurosurg Spine, 2(1), (Jan. 2005), 3-10.
Resende, et al., Local transcutaneous electrical stimulation (TENS) effects in experimental inflammatory edema and pain, European Journal of Pharmacology 504(1) (2004), 217-222.
Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).
Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).
Kwon, et al. "Translational Research in Spinal Cord Injury: A Survey of Opinion from the SCI Community," Journal of Neurotrauma, 27, pp. 21-33 (Jan. 2010).
McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).
Journal of Spinal Cord Medicine, 34(6), 620-621 (2011).
W.M. van den Bergh, et al. "Magnesium therapy after aneurysmal subarachnoid haemorrhage a dose-finding study for long term treatment," Acta Neurochir (2003) 145: 195-199.
Tang et al: "Enantioselective resolution of chiral aromatic acids by biphasic recognition chiral extraction" Tetrahedron Asymmetry, Pergamon Press Ltd, Oxford, GB LNKD-DOI:10.1016/J., Tetasy, 2007.09.031, vol. 18, No. 20, Oct. 25, 2007, pp. 2399-2408, XP022324329 ISSN: 0957-4166 abstract, Section 4.2. Extraction Experiments; p. 2406, left-hand column.
Leelarasamee N et al: "A Method for the Preparation of Polylactic Acid Microcapsules of Controlled Particle Size and Drug Loading" Journal of Microencapsulation, vol. 5, No. 2, 1988, pp. 147-158, XP002598216, ISSN: 0265-2048, p. 148, last paragraph, figure 1 p. 151, lines 16-20.
Meyer Jeffrey D et al: "Hydrophobic ion pairing: Altering the solubility properties of biomolecules" Pharmaceutical Research (New York), vol. 15, No. 2, Feb. 1998, pp. 188-193, XP002598217, ISSN: 0724-8741, p. 191, right-hand column line 55, p. 192, left-hand column, line 13, p. 192, right-hand column, lines 24-49.
International Search Report and Written Opinion for US Application PCT/US2010/028224 mailed on Sep. 14, 2010.

* cited by examiner

METHODS OF IDENTIFYING POTENTIAL COMPONENTS FOR TARGETED DRUG DELIVERY COMPOSITIONS

FIELD OF THE INVENTION

This invention relates to methods of identifying compositions for targeted drug delivery.

BACKGROUND OF THE INVENTION

Targeted delivery of therapeutic agents to specific organs is a highly challenging, exponentially developing area of experimental and translational biomedicine. In traditional drug delivery systems, after the patient is administered a therapeutic agent, the agent is distributed throughout the patients' body via the systemic blood circulation. Because only a small amount of the therapeutic agent can reach the organ on which it needs to act, a high initial dose of the therapeutic agent needs to be administered to the patient. Administering a high dose of therapeutic agent to a patient is likely to increase the systemic concentration of the therapeutic agent, which may have an adverse effect on the patient's healthy organs. If targeted delivery is successful, it would result in a significant reduction in drug toxicity, reduction of the drug dose, and increased treatment efficacy.

Accordingly, there is a need in the art for compositions that enable targeted delivery of therapeutic agents to specific organs and for methods of preparing such compositions.

SUMMARY OF THE INVENTION

In one aspect of the invention, methods of identifying potential components for compositions for preferential distribution of active agents to injury sites are provided. Such methods comprise preparing a solution comprising a delivery ligand and one or more active agents, subjecting the solution to one or more conditions to induce separation of phases in the solution, and determining whether one or more phases comprise delivery ligand-active agent complexes, which may be above a threshold concentration.

In another aspect of the invention, methods of preparing compositions for preferential distribution of active agents to injury sites are provided. Such methods comprise preparing a solution comprising a delivery ligand and one or more active agents; subjecting the solution to one or more conditions to induce separation of phases in the solution, and isolating a phase comprising delivery ligand-active agent complexes, which may be above a threshold concentration.

The delivery ligands may comprise a polymer with hydrophilic properties, while the active agent can comprise a metal ion with hydrophilic properties. Such metal ions are capable of forming complexes with the delivery ligand by forming ionic bonds through electrostatic attraction to certain heteroatoms of the ligand, for example, N, O and S atoms. The type of ionic bond can vary including electron sharing between one or more metal molecules and one or more subunits present on one or more ligand molecules. The metal counterion may also participate in the formation of the complex with the delivery ligand.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION OF THE INVENTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

In one aspect of the invention, methods of identifying potential components for compositions for preferential distribution of active agents to injury sites are provided. Such methods comprise preparing a solution comprising a delivery ligand and one or more active agents, subjecting the solution to one or more conditions to induce separation of phases in the solution, and determining whether one or more phases comprise delivery ligand-active agent complexes, which can be above a threshold concentration.

The term "injury site," as used herein, refers to an organ affected by a biological condition known to cause vessels supplying the organ to leak. Leaky blood vessels allow abnormal entrance or escape of a fluid substance such as blood and protein rich exudate from blood vessels. Biological conditions known to cause leaks in the vessels include, but are not limited to, conditions that cause swelling, such as acute and chronic inflammation; and conditions that cause angiogenesis, such as cancer and degenerative diseases including age-related macular degeneration and diabetic retinopathy.

In another aspect of the invention, methods of preparing compositions for preferential distribution of active agents to injury sites are provided. Such methods comprise preparing a solution comprising a delivery ligand and one or more active agents; subjecting the solution to one or more conditions to induce separation of phases in the solution, and isolating a phase comprising delivery ligand-active agent complexes, which can be above a threshold concentration.

A solution comprising a delivery ligand and one or more active agents may be prepared by mixing a delivery ligand and one or more active agents in a biological carrier, such as saline solution or water. The delivery ligand and one or more active agents are specifically selected so the interactions between them are mainly of an ionic nature. The interactions between the delivery ligand and the active agent may be defined as a "chelation" like effect and is based mainly on ionic interactions between the delivery ligand and the at least one active agent. For example, although polyethylene glycol (PEG) as a whole is non-ionic, the free electron pairs on the heteroatoms on the PEG chains impart an anionic character to the polymer and can bind to a cation, such as $Mg^2$.

The initial solution can comprise between about 10% to 60% of the ligand and about 0.1% to about 20% of the active agent (percent weight per volume or g of ligand or active agent/100 ml solution). The concentration of the delivery ligand in the instant compositions depends on the number of chelation sites in the delivery ligand. The delivery ligands are composed of repeating sub-units of one or more types, some of which include chelation sites. Delivery ligands with higher molecular weight are composed of a higher number of sub-units, and thus they are more likely to have more chelation sites than delivery ligands with lower molecular weight. Accordingly, as a general rule, the concentration of the delivery ligand with higher molecular weight in the composition may be lower than the concentration of the delivery ligand comprising the same sub-units and having a lower molecular weight.

Compounds suitable for use as delivery ligands in instant methods may meet the following criteria: 1) they are water soluble; 2) they are rapidly cleared from the intact blood vessels and excreted; 3) they accumulate preferentially where the blood vessels are damaged; 4) they possess hydrophilic properties; and 5) they include chelation sites suitable for binding with cations.

As noted above, it is desirable that the delivery ligands are rapidly excreted from the body when the blood vessels are intact. Accordingly, suitable delivery ligands can have a half-life less than 3 hours, less than 2 hours, or less than 1.5 hours. The rate of excretion, or half-life, of a delivery ligand is related to the molecular weight of the ligand, with higher molecular weight ligands having longer half-lives. Furthermore, for the same molecular weight, hydrophilic ligands have shorter half-lives than more hydrophobic ligands. Hydrophilic ligands that can be excreted mostly unchanged through urine have shorter half-life than ligands that requires some transformation before excretion. For example, since 24,000 DA is the cut-off for glomerular filtration, any ligand heavier than 24,000 DA needs to be degraded to some extent before it can be excreted, which adds to its half-life. Delivery ligands may be selected from polymers with hydrophilic properties having a molecular weight less than 24,000 DA.

The delivery ligand may be selected from a hydrophilic or an amphipathic polymer. The term "hydrophilic polymer," as used herein, means any macromolecule comprising of one or more repeating units, which exhibit an affinity for or attraction to water molecules, connected to each other in chained and/or branched structures. The hydrophilic polymer may be selected from synthetic or naturally occurring polymers.

Naturally occurring hydrophilic compound include, but are not limited to: proteins such as collagen and derivatives thereof, fibronectin, albumins, globulins, fibrinogen, and fibrin, with collagen particularly preferred; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; methyl cellulose, sodium carboxylmethyl cellulose and activated polysaccharides such as dextran and starch derivatives.

Useful synthetic hydrophilic agents include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), poly(polyethylene glycol methacrylate), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid, propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly (ethyloxazoline); and polyvinylamines.

The term "amphipathic polymer," as used herein, refers to any macromolecule which have localized quantum variations in charge giving rise to polar substructures and non-polar substructures. The polar substructures evidence an affinity for or attraction to other polar molecular structures such as water molecules (hydrophilic), while the nonpolar substructures exhibit an affinity or attraction for nonpolar molecules such as lipids, oils, greases, fats, etc. (lipophilic). Suitable amphipathic polymers include, but are not limited to, poloxamer P-188, polyetherester copolymers such as polyethylene glycol and polylbutylene terephthalate copolymers, polyethylene glycol and polypropylencoxide copolymers, polyethylene glycol and polypropylene glycol block copolymers.

The amphipathic polymers also include a family of polyetheramines known as Jeffamine®. These polyetheramines contain primary amino groups attached to the end of a polyester backbone, which is typically based on propylene oxide (PO), ethylene oxide (EO), or a mixture thereof. The Jeffamine® family includes monamines, diamines, triamines and secondary amines. Jeffamine® may be procured from Huntsman Corporation, headquartered in The Woodlands, Tex.

In some embodiments, the delivery ligand may comprise polyethylene glycol (PEG). PEG of molecular weights between about 200 and 24000 DA may be used or, more preferably, between about 1000 to 6000 DA are suitable for use as delivery ligands in instant compositions. PEGs of different molecular weights may be obtained from, for example, Sigma-Aldrich, St. Louis, Mo., USA.

The term "active agent," as used herein, refers to a chemical element or compound that alleviates signs or symptoms of the biological condition affecting the targeted organ and causing vessels to leak. In various embodiments, the chemical structure of the delivery ligand and the active agent is selected so they can form a complex with the delivery ligand mainly based on interactions of ionic nature.

In some embodiments, the active agent may be selected from metal ions or compounds that include such ions. Suitable active agents include, but are not limited to monovalent metal ions, such as potassium and lithium; bivalent ions, such as magnesium and calcium; transition metal ions, such as iron, zinc and copper, as well as more complex ions. Such metal ions are capable of forming complexes with the delivery ligand by forming ionic bonds through electrostatic attraction to certain heteroatoms of the delivery ligand, for example, N, O and S atoms. The type of ionic bond can vary including electron sharing between one or more metal molecule and one or more subunit present on one or more polymer molecules. The metal counterion may also participate in the formation of the complex with the delivery ligand.

In one embodiment, the active agent comprises a magnesium compound. Various magnesium salts may provide a source for the magnesium ions. Suitable magnesium salts include, but are not limited to, magnesium sulfate, magnesium carbonate, magnesium chloride, magnesium oxide and magnesium hydroxide or any combination thereof. The concentration of the active agent in the instant compositions may range between about 0.1% to about 20% weight per volume. These compounds are readily available commercially from, for example, Sigma Aldrich, St. Louis, Mo., USA.

Next, the solution is subjected to one or more conditions that induce separation of phases in the solution. Suitable conditions that may induce separation of phases may include, but are not limited to, heat, change in pH, mechanical forces including agitation, time and so forth. For example, autoclaving a solution comprising PEG and magnesium leads to formation of two liquid phases with different densities.

Whether a phase contains the delivery ligand-active agent complexes above a certain threshold may in some instances be detectable by eye. Otherwise, it can be detected using analytical methods, such as spectroscopy, microscopy, spectrometry, and so forth. If no phase has a concentration of the delivery ligand-active agent complexes above a certain threshold, the solution or the phase with the highest concentration of the delivery ligand-active agent complexes may be subjected to additional conditions to induce further separation. Similarly, after the phase with a concentration of delivery ligand-active agent complexes above a certain threshold is isolated from the rest of the solution, the rest of the solution or the phase with the next highest concentration may be subjected to more vigorous conditions. If the concentration of the delivery ligand-active agent complexes does not rise to the threshold level even after subjecting the solution to numerous conditions, it is likely that the particular combination of the delivery ligand and active agent used in the test is not suitable for instant compositions.

The phase with a concentration of delivery ligand-active agent complexes above a certain threshold is isolated from the rest of the solution. The desired phase may be isolated by filtering, micro-filtering, centrifuging, ultra-centrifuging, settling, decanting or a combination of these.

In addition to the delivery ligand and the active agents, the instant compositions may include one or more pharmaceutically acceptable carriers. The instant compositions may include excipients such as solvents, binders, fillers, disintegrants, lubricants, suspending agents, surfactants, viscosity increasing agents, buffering agents, antimicrobial agents, among others. Many different pharmaceutically acceptable carriers and excipients are known and disclosed, for example, in Remington's Pharmaceutical Sciences, Lippincott Williams & Wilkins; 21 edition (May 1, 2005).

In some embodiments, the instant compositions are prepared for parenteral administration. Parenteral administration is generally characterized by a subcutaneous, intramuscular, or intravenous injection. Instant compositions for parenteral administration may be prepared as liquid solutions or solid forms suitable for solution prior to injection.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. A method of preparing compositions for distribution of active agents, the method comprises:
   preparing a solution comprising a delivery ligand and one or more active agents, wherein the delivery ligand comprises polyethylene glycol (PEG), and the solution comprises the delivery ligand in an amount of between about 30% and about 40% w/v, and the one or more active agents comprises a magnesium compound in an amount of 0.8% w/v;
   subjecting the solution to one or more conditions to induce separation of phases in the solution; and
   isolating a phase comprising delivery ligand-active agent complexes.

2. The method of claim 1, wherein the isolated phase has a highest concentration of delivery ligand-active agent complexes.

3. The method of claim 1, wherein the delivery ligand and the one or more active agents are selected so the interaction between them is of an ionic nature.

4. The method of claim 1, wherein the magnesium compound comprises a magnesium ion.

5. The method of claim 1, wherein the PEG comprises PEG of molecular weights between about 1,000 to 6,000 Da.

6. The method of claim 1, wherein the magnesium compound comprises a magnesium salt.

7. The method of claim 1, wherein the magnesium compound comprises magnesium sulfate, magnesium carbonate, magnesium chloride, magnesium oxide or magnesium hydroxide.

8. The method of claim 1, wherein the magnesium compound comprises magnesium sulfate.

9. The method of claim 1, wherein the magnesium compound comprises magnesium carbonate.

10. The method of claim 1, wherein the magnesium compound comprises magnesium chloride.

11. The method of claim 1, wherein the magnesium compound comprises magnesium oxide.

12. The method of claim 1, wherein the magnesium compound comprises magnesium hydroxide.

* * * * *